US010561512B2

(12) United States Patent
Willard

(10) Patent No.: US 10,561,512 B2
(45) Date of Patent: Feb. 18, 2020

(54) ADJUSTABLE WALKING SOLE FOR AN ORTHOSIS

(71) Applicant: Orthomerica Products, Inc., Orlando, FL (US)

(72) Inventor: Benjamin R. Willard, Casselberry, FL (US)

(73) Assignee: ORTHOMERICA PRODUCTS, INC., Orlando, FL (US)

( * ) Notice: Subject to any disclaimer, the term of this patent is extended or adjusted under 35 U.S.C. 154(b) by 769 days.

(21) Appl. No.: 15/237,319

(22) Filed: Aug. 15, 2016

(65) Prior Publication Data

US 2017/0049601 A1 Feb. 23, 2017

Related U.S. Application Data

(60) Provisional application No. 62/207,222, filed on Aug. 19, 2015.

(51) Int. Cl.
| | | |
|---|---|---|
| *A61F 5/01* | (2006.01) | |
| *A43B 3/24* | (2006.01) | |
| *A43B 7/24* | (2006.01) | |
| *A43B 13/14* | (2006.01) | |

(52) U.S. Cl.
CPC ............ *A61F 5/0111* (2013.01); *A43B 3/244* (2013.01); *A43B 3/246* (2013.01); *A43B 7/24* (2013.01); *A43B 13/14* (2013.01); *A61F 5/0127* (2013.01); *A61F 5/0195* (2013.01); *A61F 2005/0158* (2013.01); *A61F 2005/0197* (2013.01)

(58) Field of Classification Search
CPC .... A61F 5/0111; A61F 5/0195; A61F 5/0127; A61F 2005/0158; A61F 2005/0197; A43B 13/14; A43B 3/246; A43B 3/244; A43B 7/24
See application file for complete search history.

(56) References Cited

U.S. PATENT DOCUMENTS

| | | | | |
|---|---|---|---|---|
| 2,616,190 | A | | 11/1952 | Darby |
| 3,377,723 | A | * | 4/1968 | England ................. A43B 5/001 36/39 |
| 3,777,747 | A | * | 12/1973 | Friedman .............. A61F 5/0193 602/24 |
| 4,040,416 | A | * | 8/1977 | Zentman ............... A61F 5/0193 602/24 |

(Continued)

FOREIGN PATENT DOCUMENTS

FR 2534804 4/1984

OTHER PUBLICATIONS

International Search Report and Written Opinion of the International Searching Authority dated Nov. 17, 2016 for Corresponding International Patent Application No. PCT/US2016/047198, filed Aug. 16, 2016.

(Continued)

*Primary Examiner* — Tarla R Patel

(57) ABSTRACT

An ankle/foot orthosis includes an orthosis boot that is attached to an adjustor unit that positions a sole offset from the orthosis boot. The adjuster unit provides angular adjustments of an inclination of the sole relative to the orthosis boot to accommodate a specific condition of the user's foot by rotation of wedged rotary plates to provide corrective alignment of the user's foot relative to a support surface during walking.

12 Claims, 18 Drawing Sheets

(56) References Cited

U.S. PATENT DOCUMENTS

| | | | |
|---|---|---|---|
| 4,157,876 A | | 6/1979 | DiGiulio |
| 4,336,795 A | * | 6/1982 | Nichols ................ A61F 5/0193 602/24 |
| 5,470,310 A | * | 11/1995 | Sutcliffe .............. A61F 5/0193 128/882 |
| 7,112,181 B1 | | 9/2006 | Detoro et al. |
| 2006/0277772 A1 | | 12/2006 | Pupko |
| 2007/0073206 A1 | | 3/2007 | Hatton et al. |
| 2011/0021963 A1 | | 1/2011 | Graddon et al. |
| 2011/0192051 A1 | * | 8/2011 | Wadman ............. A43B 3/0042 36/88 |
| 2012/0151803 A1 | * | 6/2012 | Selner ...................... A61F 5/14 36/144 |

OTHER PUBLICATIONS

Extended European Search Report (completion date Jun. 27, 2018) for Corresponding European Patent Application No. 16837702.6, filed Jan. 26, 2018.

International Preliminary Report on Patentability dated Mar. 1, 2018 for Corresponding International Patent Application No. PCT/US2016/047198, filed Aug. 16, 2016.

\* cited by examiner

ADJUSTABLE WALKING SOLE FOR AN ORTHOSIS

CROSS-REFERENCE TO RELATED APPLICATIONS

This application claims priority to U.S. Provisional Application No. 62/207,222 filed on Aug. 19, 2015, the entire contents all of which are incorporated herein by reference.

BACKGROUND OF THE INVENTION

Patients with a compromised ankle/foot resulting from a chronic illness, diabetes mellitus, Charcot joints or even limited mobility or advanced age can be subject to pressure ulcers caused by ischemia, direct trauma and/or repetitive stress. Frequently such patients may suffer from decreased sensation and/or paralysis of the ankle/foot. Various forms of orthotics have been provided as a neuropathic ankle/foot orthoses. Such products have attempted to provide a smooth and efficient pattern of walking with enhanced mobility and functional activities for a patient. At the same time, they attempt to protect the entire foot and ankle structures while reducing loading and shearing forces. Usually such orthotics seek to establish a plantigrade alignment of the deformed foot and ankle structures while utilizing pressure and shear-dissipating materials. Such orthotics are frequently custom made to address relief of, for example, a diabetic foot ulcer in pressure-sensitive areas by establishing support in pressure-tolerant areas of the foot. The foot/ankle can be encompassed within a boot-like structure and a rocker sole can be customized to reduce load bearing forces to the metatarsal heads of the foot. Diabetes is a major factor in lower extremity amputations in the United States and regretfully, diabetics suffer a lack of feeling in the foot, poor circulation, foot deformities, irritation and trauma. Patients who have had diabetes for a number of years can develop neuropathy with a reduced or complete lack of ability to feel pain in the feet due to nerve damage caused by elevated blood glucose levels over time.

When an orthotist or a podiatrist determines that an orthotic is necessary to cover the wound and ulcers to prevent a risk of infection, they have frequently had to customize the bottom configuration of the exterior sole to provide appropriate lateral and interior/posterior angular adjustments to accommodate the specific needs of the patient. Frequently a low profile rocker sole is utilized to reduce load-bearing forces to the metatarsal heads of the foot, and the orthotist/podiatrist may have to grind and sand the sole of the orthotic in an attempt to create particularly desired angular adjustments necessary for the particular condition of the patient.

SUMMARY OF THE INVENTION

The present invention addresses laborious prior art requirements of adjusting an ankle/foot orthosis boot to meet the subject requirements of a patient's foot. This is accomplished with an adjustable walking sole that is projected below the bottom of an ankle/foot orthosis boot that permits with the loosening and tightening of a single bolt with a nut to vary an inclination or tilt of the boot relative to a rigid foot plate that supports a contact sole. An outside plate carrying both an indicator and a window is mounted below an attachment plate that connects directly with the bottom of an ankle/foot orthosis boot. An adjuster unit having a pair of wedged rotary plates, that include spring washers, are mounted to enable relative rotation to enable adjustments of a tilt of the boot to accommodate the needs of a particular patient. Slots and circumferential complementary protrusions can maintain a patient adjustment by simply tightening a nut on a bolt that is recessed from a surface of a sole mounted on a lower surface of a rigid foot plate. The window is provided to enable a practitioner to set an appropriate tilt while the indicator can be aligned with markings on an upper surface of a rigid foot plate to enable the practitioner to also maintain the sole in a forward plane of a walking gait progression, even if the patient's foot is misaligned or deformed to be pointed in a different direction.

The open space between the boot and the upper surface of the rigid foot plate can be provided with a protective shield or guard to avoid any inadvertent catching of an extraneous article that could trip the patient between the lower surface of the boot and the upper surface of the rigid foot plate.

BRIEF DESCRIPTION OF THE VARIOUS EMBODIMENTS

The objects and features of the present invention, which are believed to be novel, are set forth with particularity in the following description. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
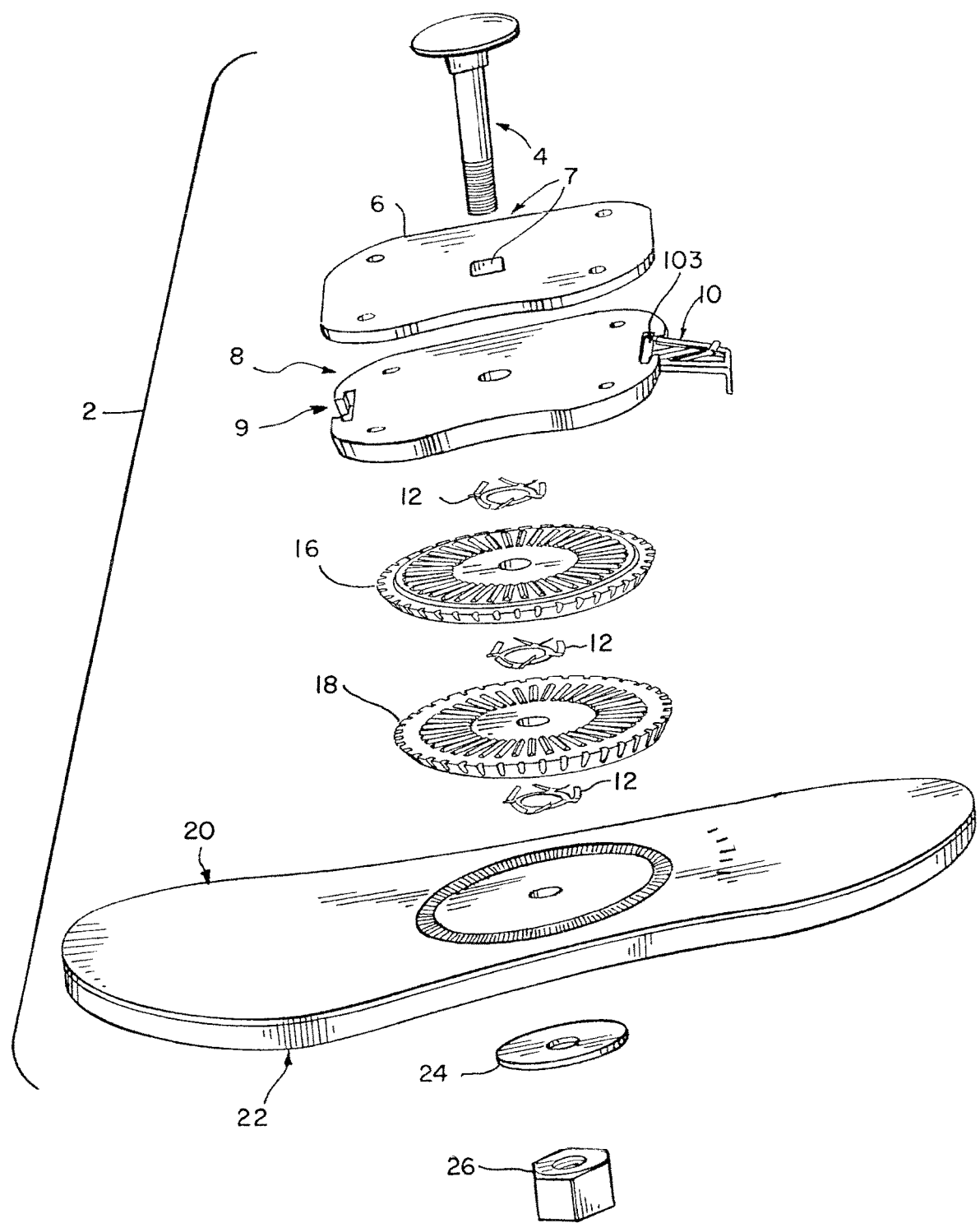
FIG. 1 (Part 1) is an exploded view of components of an adjustable walking sole.
Figure 2:
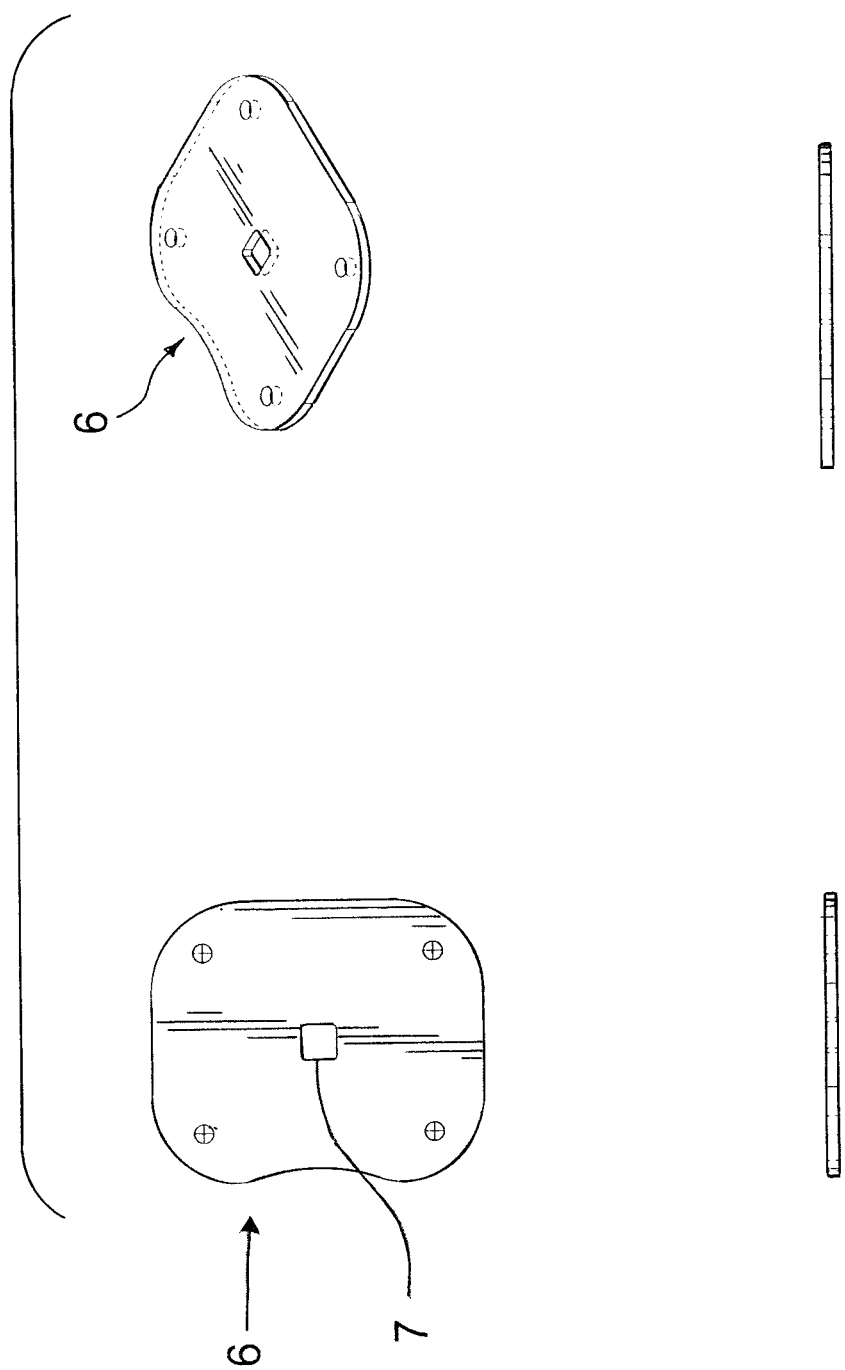
FIG. 2 (Part 2) are views of an attachment plate in an upper view, a perspective view and respective side views.

Referring to FIG. 1 (Part 1), an exploded view of the components of an adjustable walking sole 2 is disclosed. A bolt 4 with a relatively flat upper disk surface can be secured through a rectangular hole 7 to an attachment plate 6 that matches a corresponding upper bolt shaft rectangular portion that is above the circular threaded shaft of the bolt 4. The attachment plate 6 can be connected through an appropriate set of four screws to a bottom of an ankle/foot orthosis boot 3 to support a patient's foot.

An outside plate 8 is also fixed to the bottom of an ankle/foot orthosis boot 3 by the same four screws. An aluminum plate (not shown) can be mounted on an inside bottom of an ankle/foot orthosis, such as a boot 3 configured to match the condition of the patient's ankle/foot, to receive the four screws and secure the bottom of the ankle/foot orthosis 2 between the aluminum plate and the attachment plate 6.

Figure 3:
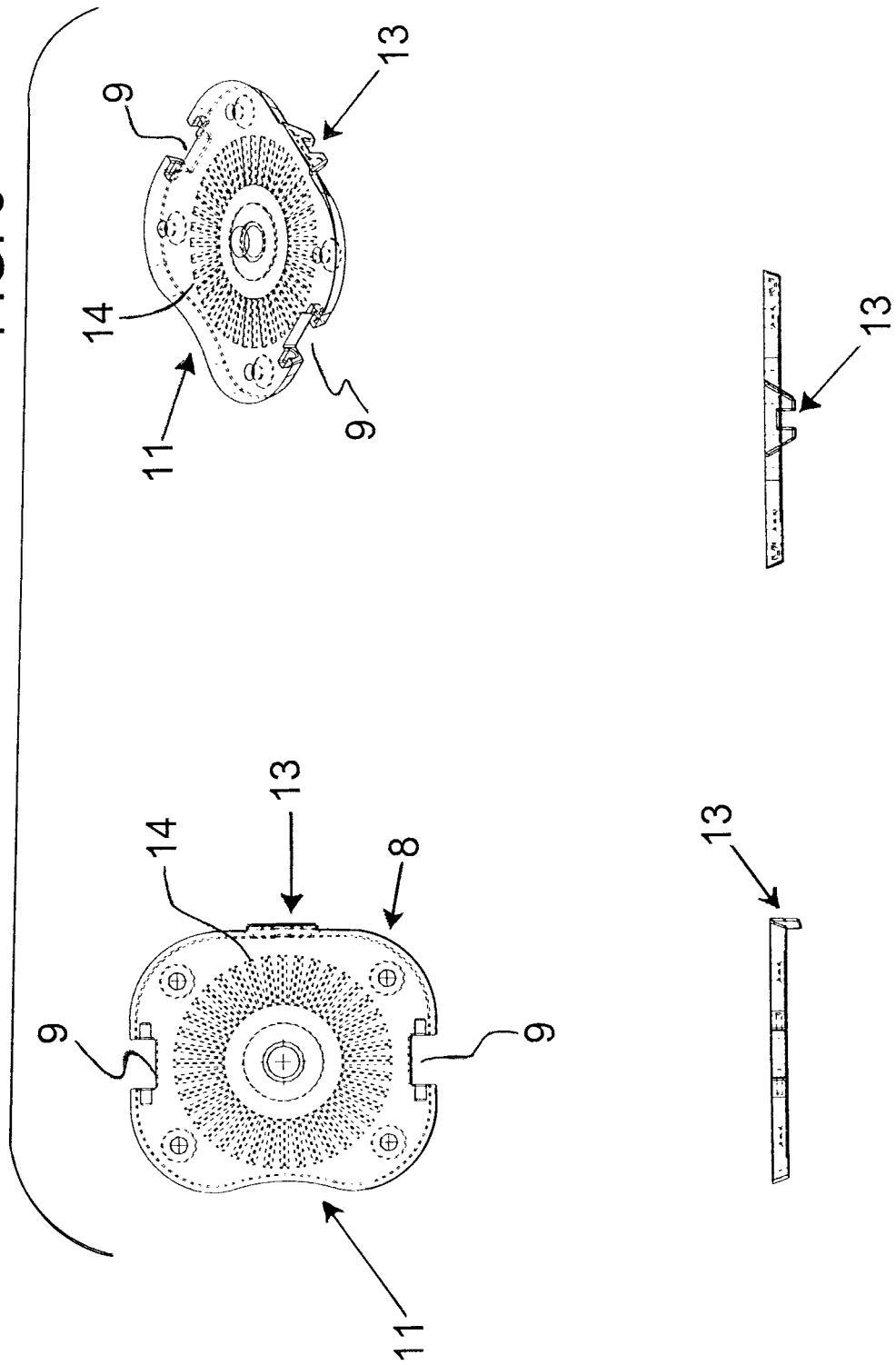
FIG. 3 (Part 3) are drawings of an outside plate with an indicator window in an upper view, a perspective view and side views.
Figure 4:
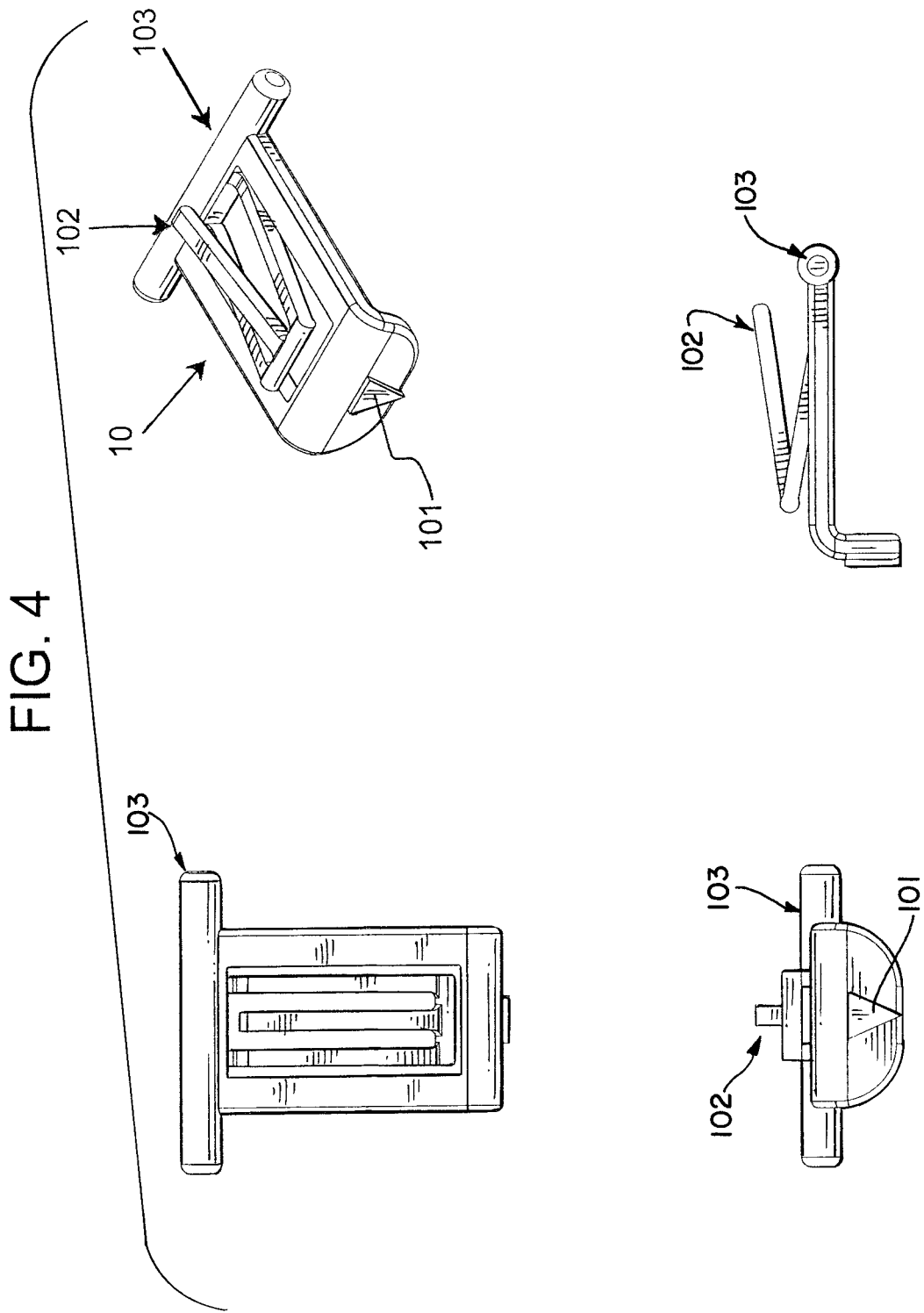
FIG. 4 (Part 4) are views of an indicator component that can be mounted at either end of the outside plate in an upper view, a perspective view and side views.

As can be seen in FIG. 3, a pair of identical recesses 9 are aligned along a longitudinal axis on opposite perimeter surfaces of the attachment plate 6 and are capable of releasably mounting an indicator 10, as shown in FIG. 4, which can be removably mounted in either one of the recesses 9 on the attachment plate 6.

In FIG. 3, on a left hand side, a perimeter concavity 11 is provided to define a matching location of a medial inside of a foot of a patient. Alternative forms of notches can be used to provide an alignment with a right or left foot. On the other side of the outside plate 8 is a window indicator 13 that extends downward to provide a square opening to display the markings on the edges of an upper wedged rotary plate 16 and a lower wedged rotary plate 18. The underside of the outside plate 8 has a series of wedged slots 14 radiating outward from a center to form a composite circular configuration for attachment to an upper wedged rotary plate 16.

FIG. 4 discloses a removable indicator 10 having at one end a triangular narrow head configuration 101 extending down below the outside plate 8 to indicate a position relative to angular markings (not shown) on an upper surface of a rigid foot plate 20. At the other end of the indicator 10, a cylindrical bar 103 is dimensioned to be mounted within one of the recesses 9 located at either end of the outside plate 8. The indicator 10 has a central rectangular opening with a spring member 102 extending upward to provide a bias force for holding the indicator 10 within one of the recesses 9 when the outside plate 10 is fastened to the attachment plate 6. The position of the indicator 10 can be switched to accommodate a right foot or a left foot of a patient with a medial concavity 11 positioned on the inside of the patient's foot and the indicator 10 is aligned with angular markings on an outer surface of the rigid foot plate 20 to assist in aligning the rigid foot plate 20 to address a corrective alignment of the patient's foot relative to a support surface.

Figure 7:
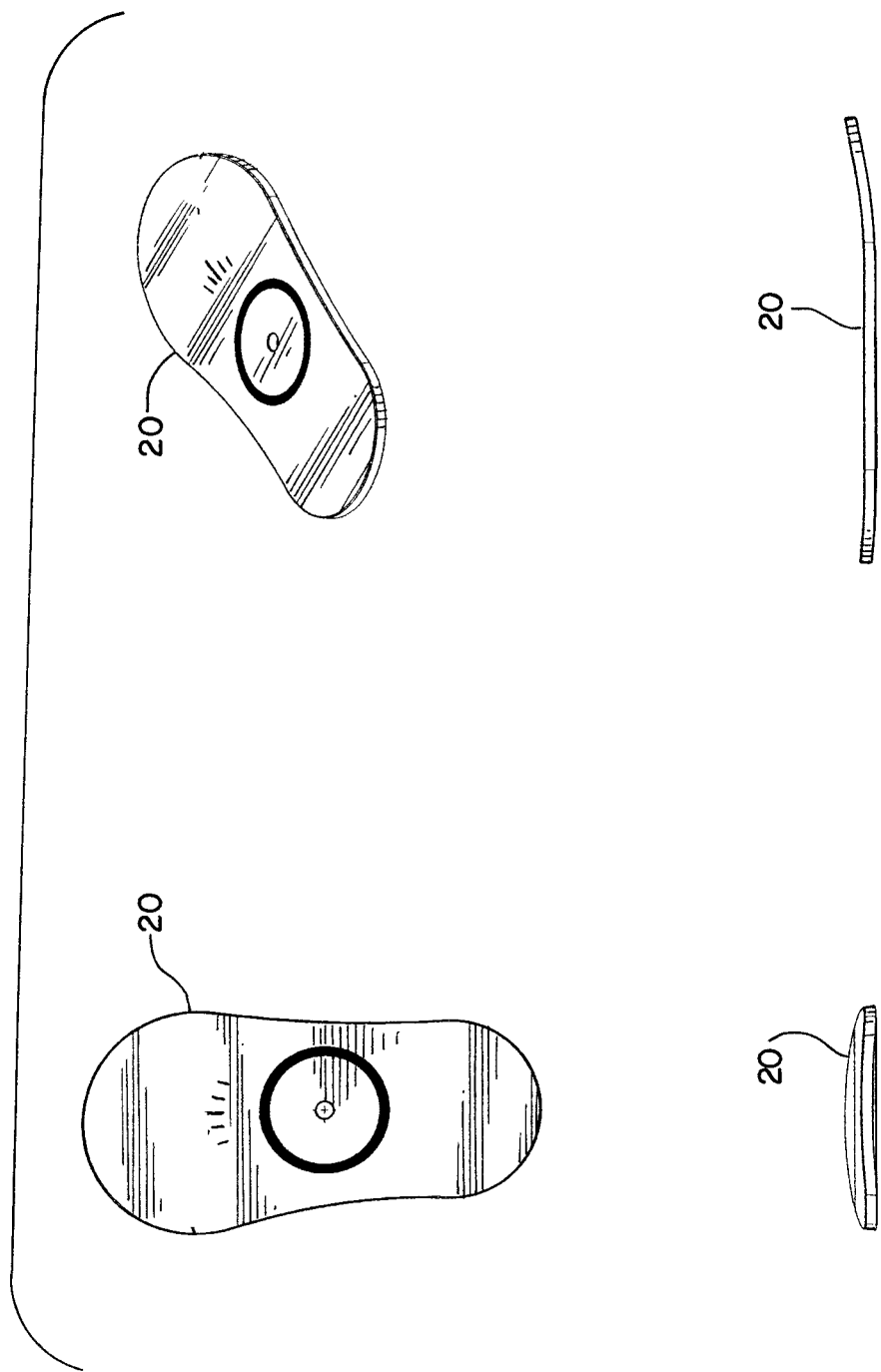
FIG. 7 (Part 7) are views of a rigid foot plate in an upper view, a perspective view, and side views.

Generally a medical practitioner will use a Goniometer to measure the patient's foot alignment and the markings 23 on the outer surface of the rigid foot plate 20 (see FIG. 7) can coordinate with the Goniometer measurements so that the rigid foot plate 20 will be aligned parallel to the direction the patient is walking, even if the patient's foot is deformed and extends at an angle to that walking direction with the boot 3 accommodating the alignment of the patient's foot.

Figure 5:
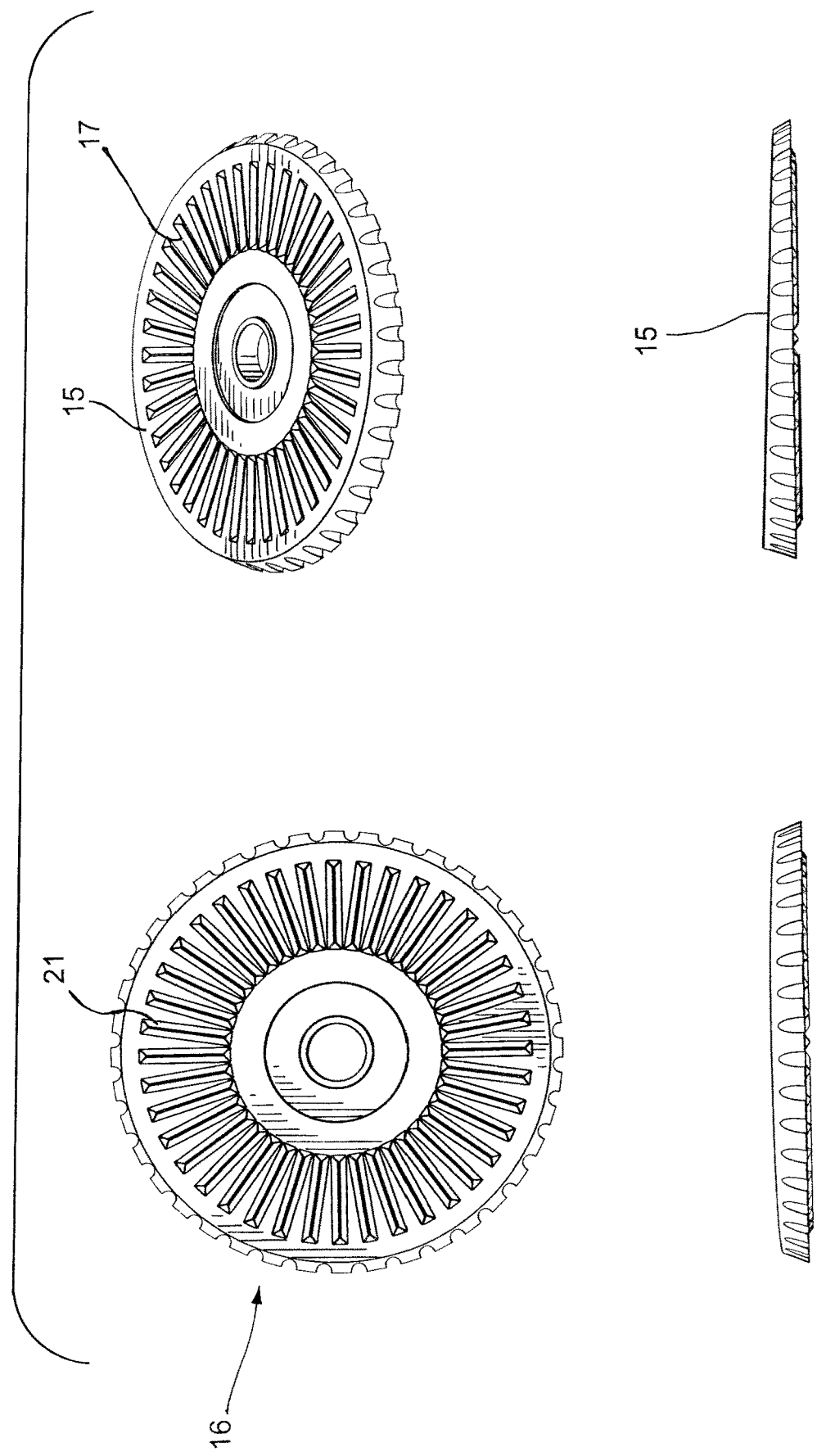
FIG. 5 (Part 5) are views of an upper wedged rotary plate in an upper view, a perspective view and side views.

FIG. 5 discloses various views of an upper wedged rotary plate 16 that can be manufactured from a machined or stamped metal plate or from a plastic material in an appropriate mold, or printed by plastic resin from a manufacturing 3D printer. The lower surface 15 is inclined relative to a plane of an upper surface of the wedged rotary plate 16 and has a series of circumferential wedged slots 17 that will be complementary to protrusions 21 of a wedged configuration extending upward from the top of the lower wedged rotary plate 18. The upper surface of the upper wedged rotary plate 16 has a series of protruding wedged-shaped projections 21 extending radially outward and complementary to the wedged slots 19 on the bottom of the outside plate 8. The wedged slots and protruding wedged-shaped projections are complementary in shape and dimension to permit a locking engagement between the respective upper and lower rotary plates.

Figure 6:
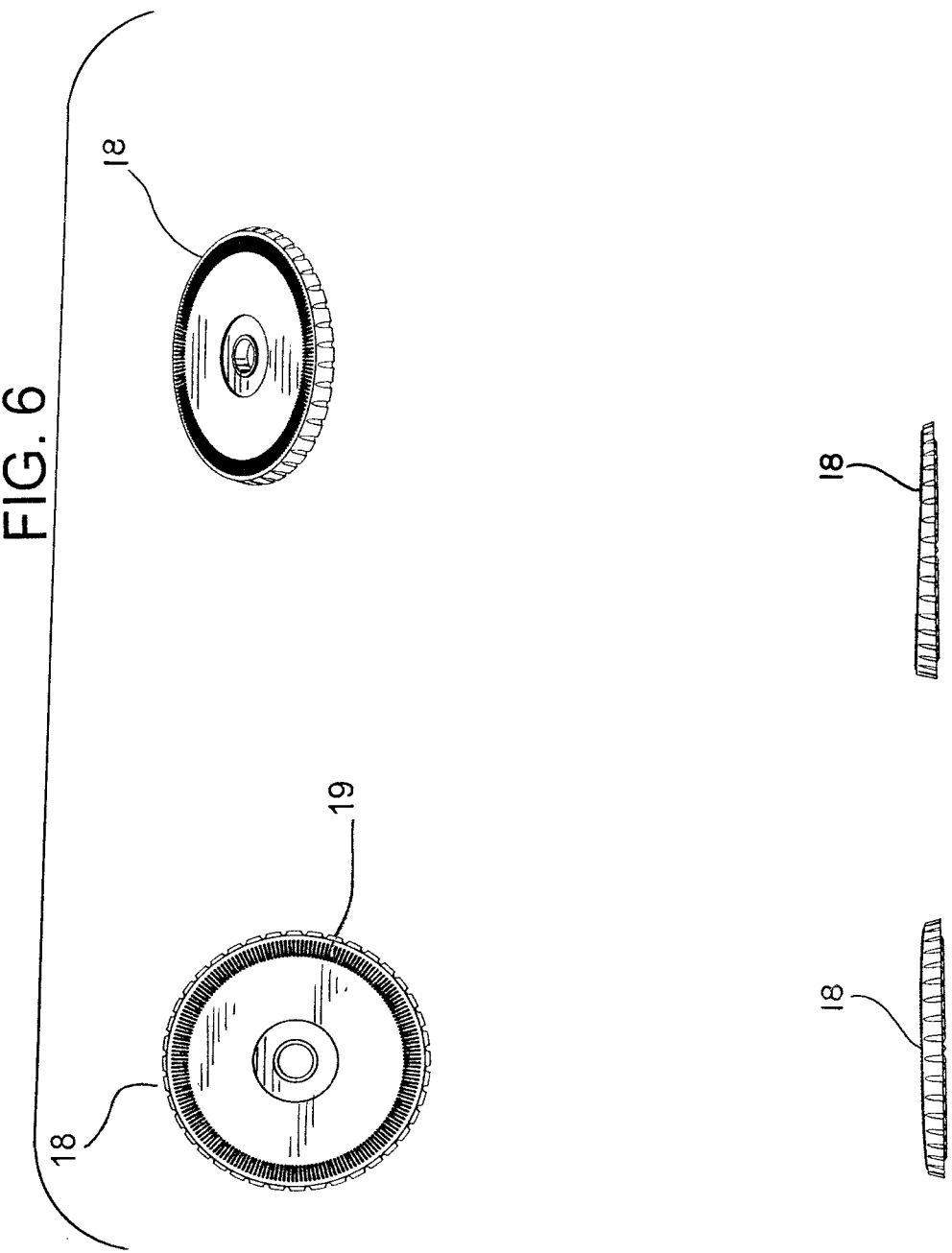
FIG. 6 (Part 6) are views of a lower wedged rotary plate in an upper view, a perspective view and side views.

Three spring washers 12 such as Finger Washers made of a high carbon steel, each having six cantilevered fingers, are provided with a central opening that accommodates the circumference of the bolt 4. The spring washers 12 are mounted respectively, one between the outside plate 8 and the top of the upper wedged rotary plate 16 while a second spring washer 12 is mounted between the lower surface of the upper wedged rotary plate 16 and the upper surface of the lower wedged rotary plate 18 (see FIGS. 1 and 6). Finally, a third spring washer 12 is mounted between the lower surface of the lower wedged rotary plate 18 and the top of rigid foot plate 20. The spring washers 12 help separate the upper wedged rotary plate 16 and the lower wedged rotary plate 18 when the bolt 4 is loosened, to permit relative rotation for adjusting an angular alignment of the wedged rotary plates to meet the alignment requirements of the patient's foot.

The lower wedged rotary plate 18 has a circular pattern of slots 19 that extend adjacent the perimeter of the lower wedged rotary plate 18. The rigid foot plate 20 has on its surface and surrounding the hole that receives the bolt 4, a complementary series of slots 21 to interact with and fasten the lower wedged rotary plate 18 to the top of the rigid foot plate 20.

As can be seen in FIG. 1, a washer 24 is mounted at the bottom of the rigid foot plate 20 with a nut 26 bearing upon the washer 24 and capable of being threaded on the bolt 4 for holding fast to the bolt 4.

In FIG. 1, the rigid foot plate 20 has a rubber-like sole 22 fastened, for example by glue, to the bottom surface of the rigid foot plate 20. As can be appreciated, other appropriate surface contact soles can be utilized apart from rubber.

Figure 8:
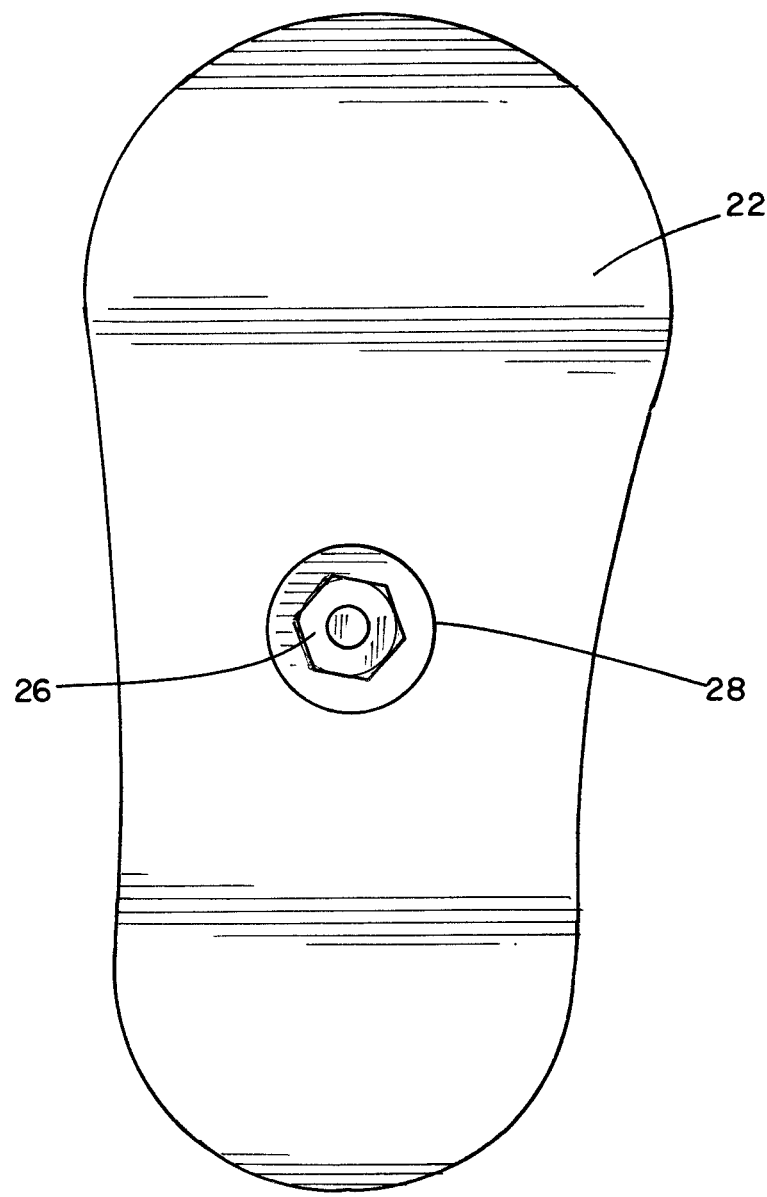
FIG. 8 (Part 8) is a bottom view of the rigid foot plate with a washer and nut attaching a bolt and a bottom surface supporting a rubber sole.

FIG. 8 is a bottom view of the rigid foot plate 20 with a circular concavity 28 provided with sufficient clearance to permit a tool to attach to and rotate the bolt 4. The concavity 28 is in the sole member 22.

Figure 9:
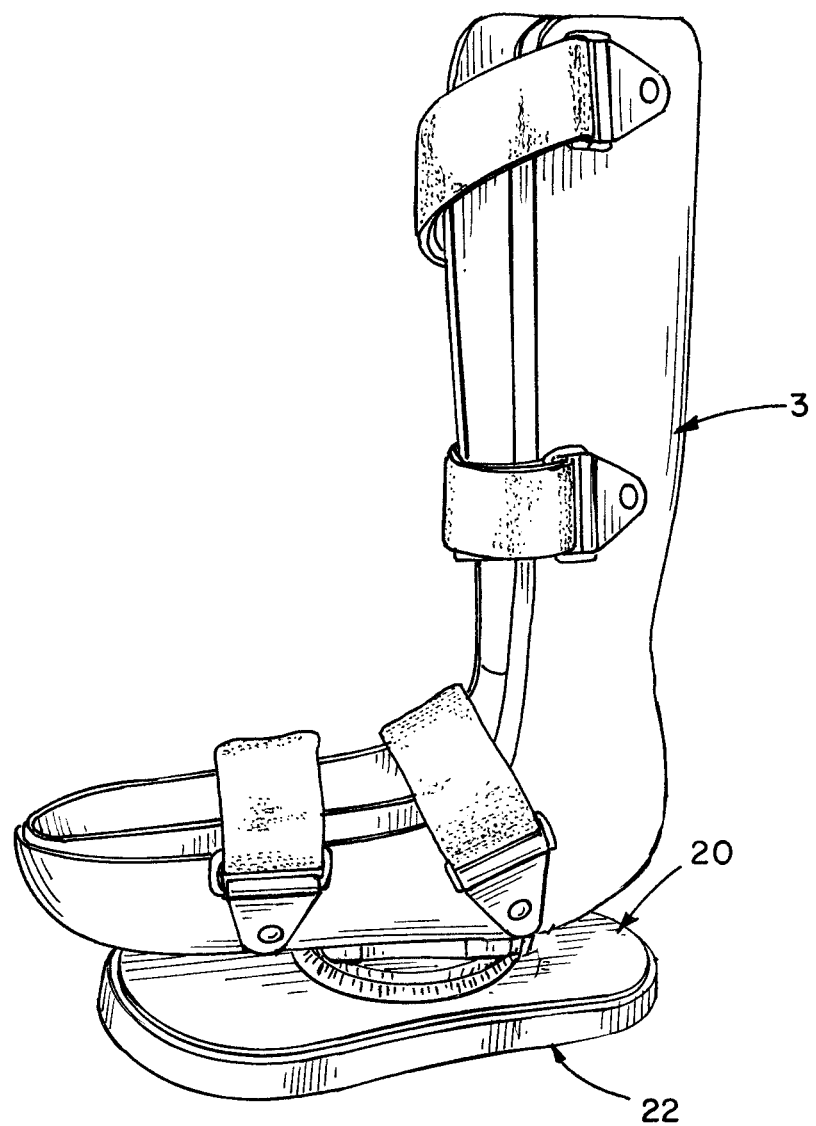
FIG. 9 is a perspective side view of an ankle/foot orthosis mounted on an adjustable sole with offset longitudinal axes between the orthosis and the sole.

FIG. 9 is a side perspective view of an ankle/foot orthosis with a patient boot 3 attached to the adjustable walking sole 2.

Figure 10:
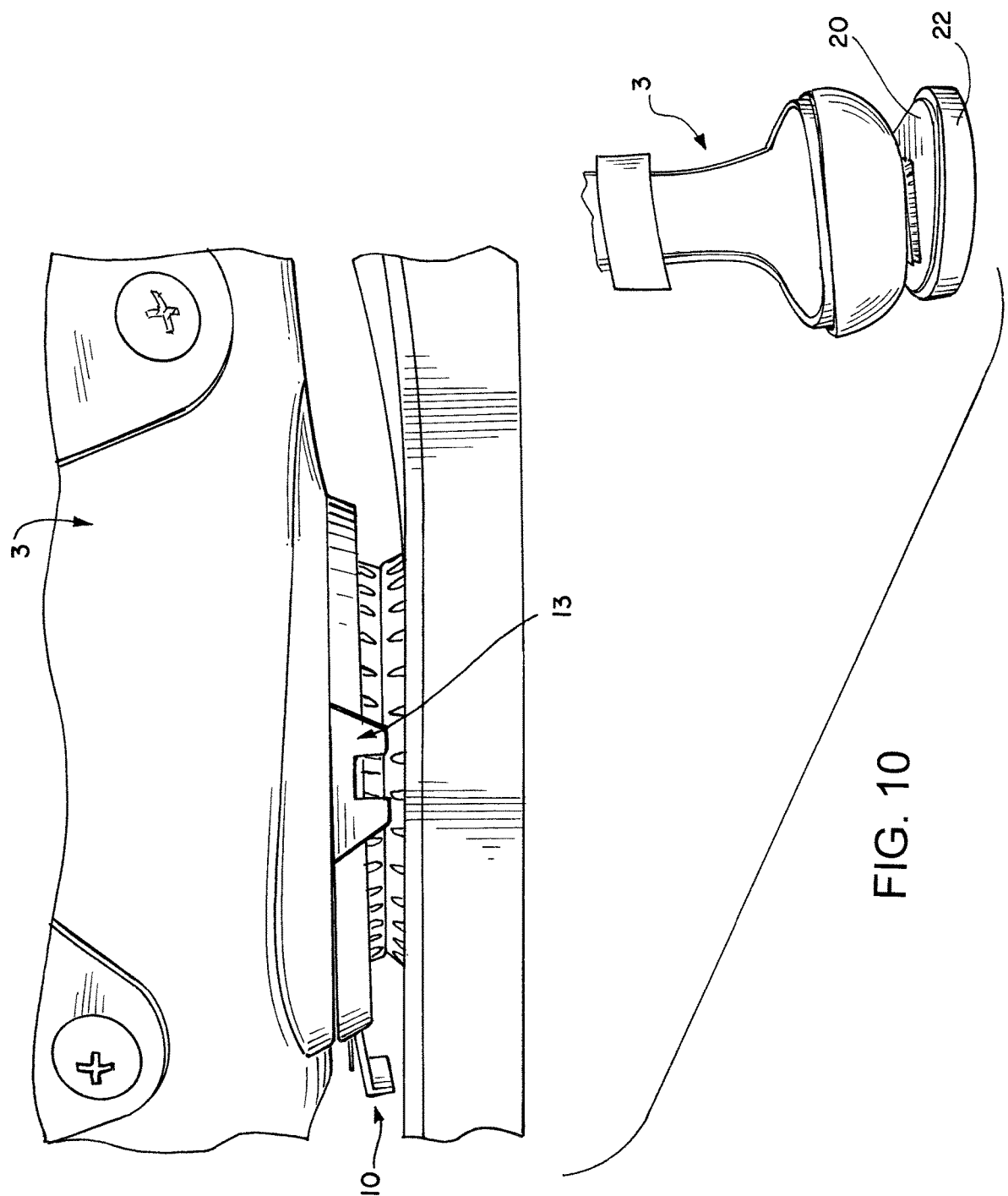
FIG. 10 is a partial side view disclosing the window for a desired angle number and a separate back view showing an inclination angle of the ankle/foot orthosis relative to the foot plate.

FIG. 10 discloses the indicator window 13 on the outside plate 8, positioned at a 90° offset from the indicator 10.

The number of slots and complementary protrusions between the upper wedged rotary plate 16 and the lower edge rotary plate 18 can be 52 which is approximately a 7° angular displacement between each slot and each projection. As can be appreciated, an alternative number of slots and projections could be utilized. The upper surface of the upper wedged rotary plate 16 is flat with indented slots while the lower surface of the lower wedged rotary plate 18 is flat with projections. The outer perimeter edges of the respective upper wedged rotary plate 16 and lower wedged rotary plate 18 have respectively, from a middle point of 0, to offset of +6 on one side and an offset of a −6 on the other side. The lower wedged rotary plate is also marked with a 0 but extends to a −6 to provide a matched complement of the +6 of the upper wedged rotary plate 16. Conversely, on the other side of 0 the lower wedged rotary plate extends from a −1 to a −6 to align with the +1 to +6 of the upper wedged rotary plate 16.

When the respective upper rotary plate 16 and lower rotary plate 18 are matched in window 13 with a 0 above a 0, the alignment of the protrusions and slots provide a constant thickness across the full combination of the upper wedged rotary plate 16 and a lower edge rotary plate 18. Accordingly, if there is no desired inclination, the ankle/foot orthosis boot 3 will be aligned as mentioned above and not tilted relative to the rigid foot plate 20 at the top of the sole 22.

The adjustor unit includes the upper wedged rotary plate 16 and the lower wedged rotary plate 18 along with the mounting attachment plate 6, outside plate 8, rigid foot plate 20, washer 24, nut 26 and bolt 4. The spring washers 12 facilitate relative rotations of the rotary plates 16 and 18.

The orthotist or the podiatrist can utilize a chart indicating the degree of tilt that is desired for the particular needs of a patient and can loosen the bolt 4 and respectively rotate the upper wedged rotary plate 16 and the lower wedged rotary plate 18 so that the −6 and the +6 align and only the lower 0 is shown in the window. This gives the maximum tilt to the patient.

Figure 11:
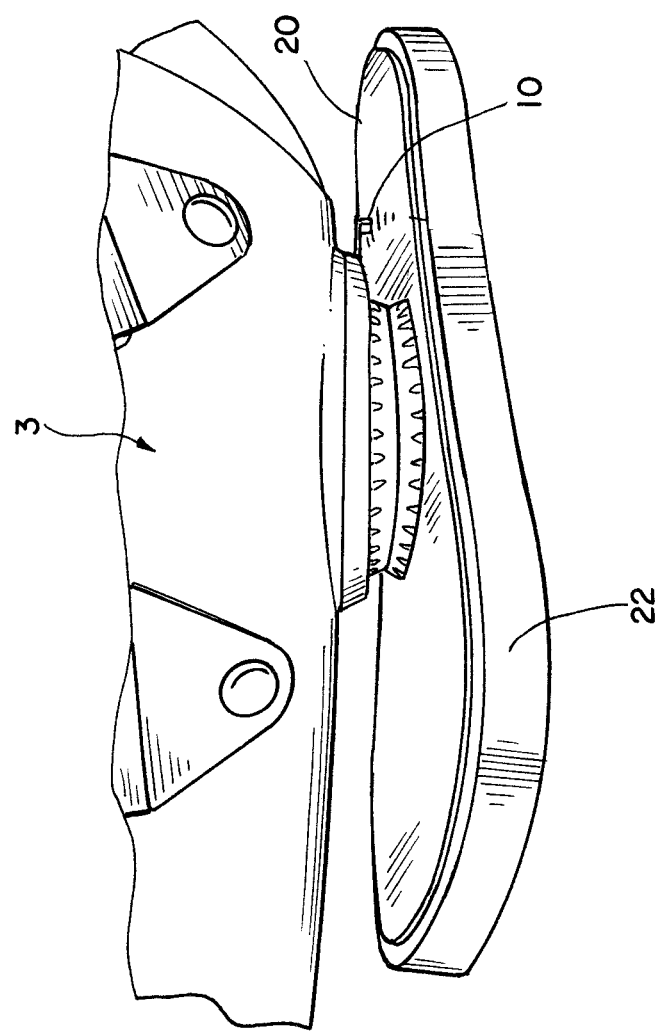
FIG. 11 is a side perspective view of the foot plate and upper and lower wedged rotary plates with a foot plate set to maintain the sole of the rigid foot plate in a forward plane of gait progression of the patient to compensate for deviation of the patient's foot.

As can be seen in FIG. 11, the indicator 10 can be utilized to alter the relationship of the foot plate 20 relative to the alignment of the ankle/foot orthosis boot 3 when the bolt 4 has been loosened.

Figure 12:
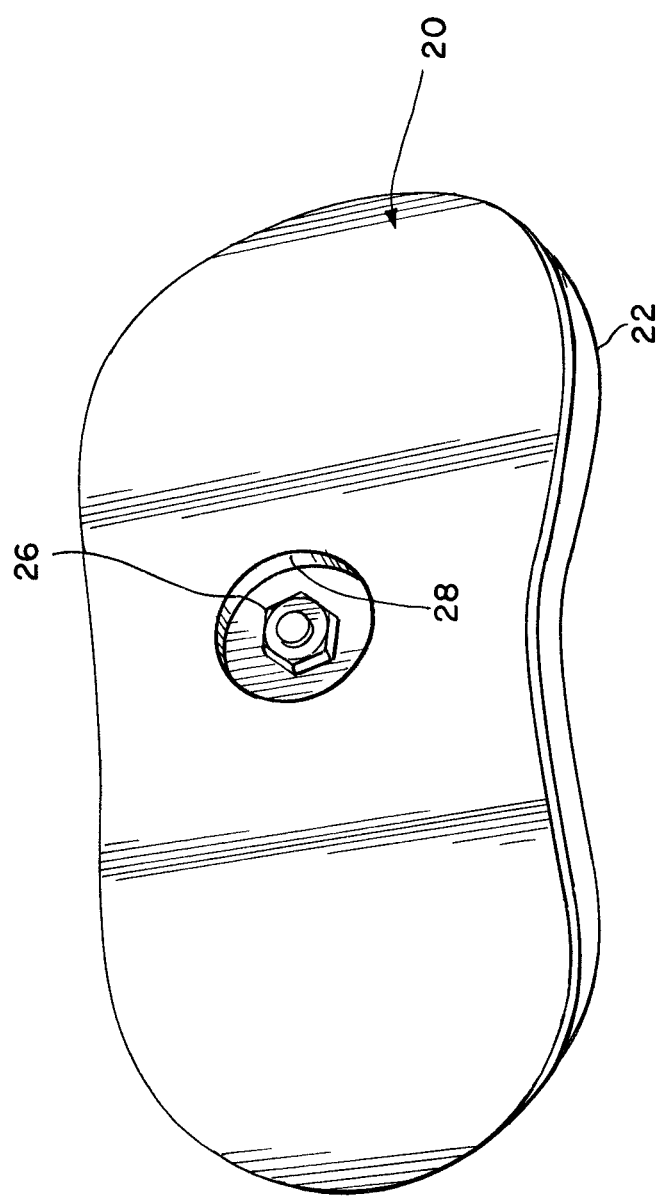
FIG. 12 is a bottom perspective view of a rubber like sole mounted on the rigid foot plate with a single bolt and nut fastened in a recess to maintain the desired angles.

As can be seen in FIG. 12, the adjustments can be made without requiring any grinding or replacement of soles by loosening the bolt 4 and setting an appropriately desired tilt with regards to the wedged plates 16 and 18 and also aligning the sole 22 to be positioned in the forward plane of a gait progression, even if the patient's foot and boot 3 point in a different direction.

Figure 13:
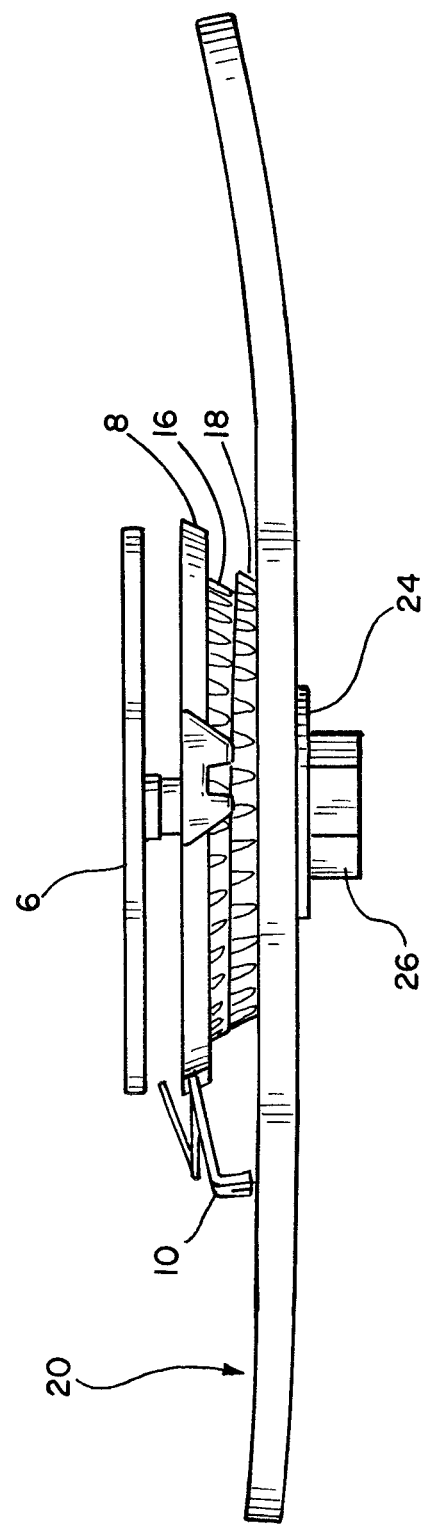
FIG. 13 is a side view of the components of the adjustable walking sole without the ankle/foot orthosis.

FIG. 13 is a side profile of an adjustable walking sole without a glued on sole fixed to the rigid foot plate 20.

Figure 14:
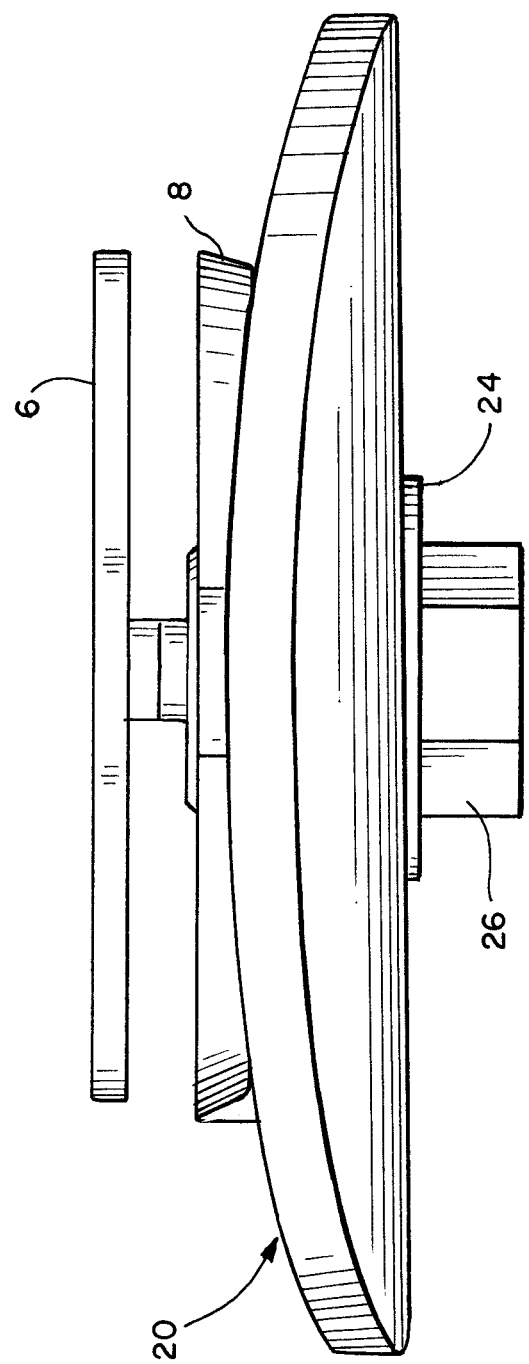
FIG. 14 is a front view of the components of the adjustable walking sole without the ankle/foot orthosis.
Figure 15:
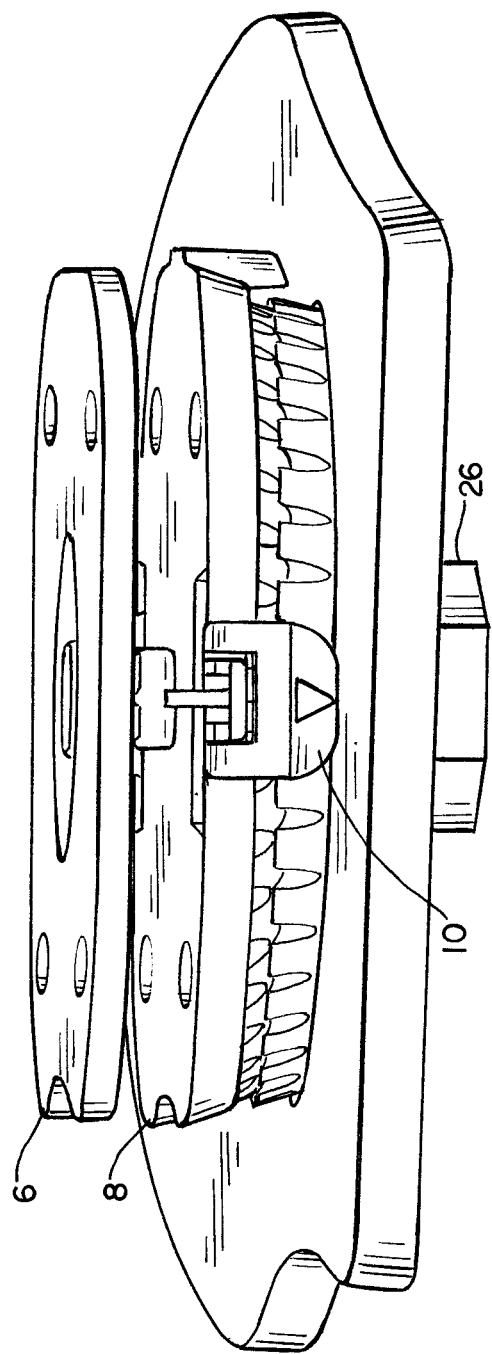
FIG. 15 is a rear view of the components of the adjustable walking sole without the ankle/foot orthosis.

FIG. 14 is a front view of the adjustable walking sole 2 while FIG. 15 is a rear view.

Figure 16:
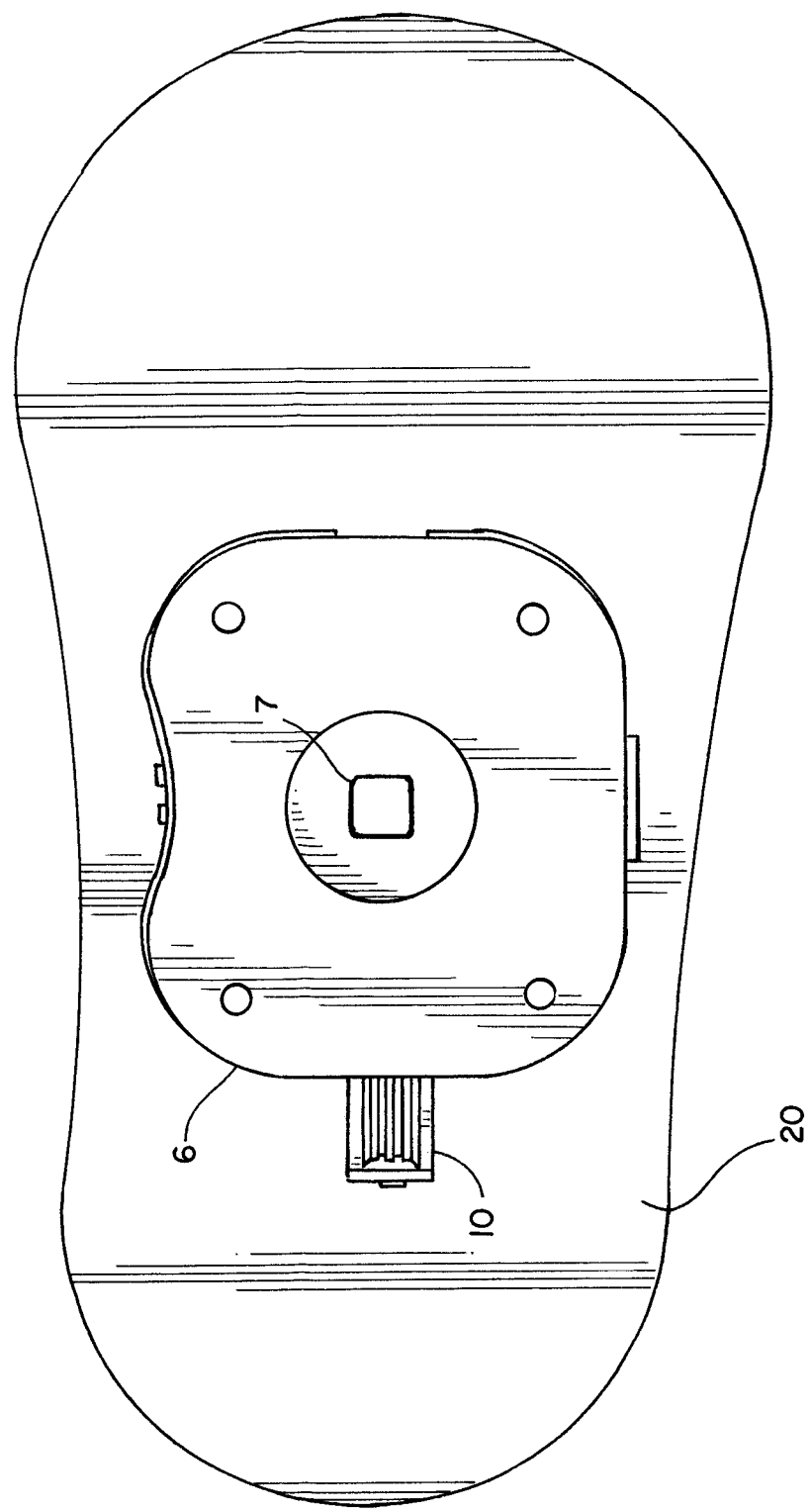
FIG. 16 is a top view of the components of the adjustable walking sole without the ankle/foot orthosis.

FIG. 16 is a top view of the adjustable walking sole 2.

FIG. 11 discloses a relationship between the indicator 10 and the surface of the rigid foot plate 20. Markings not shown on the surface of the rigid foot plate 20 permits the practitioner to alter the rotational angle of the foot plate 20 to maintain the sole 22 in the forward plane of gait of progression of the patient when walking, even if the actual foot has been deformed to point in a different direction during the progression of the patient.

FIG. 12 shows the sole 20 with a circular concavity 26 that permits a tool to loosen or tighten the nut 26 on the threaded bolt 4.

FIG. 13 is a side view of the adjustable walking sole 2.

FIG. 14 is a front view of the adjustable walking sole 2.

FIG. 15 is a rear view of the adjustable walking sole 2.

FIG. 16 is a top view of the components of the adjustable walking sole 2.

Figure 17:
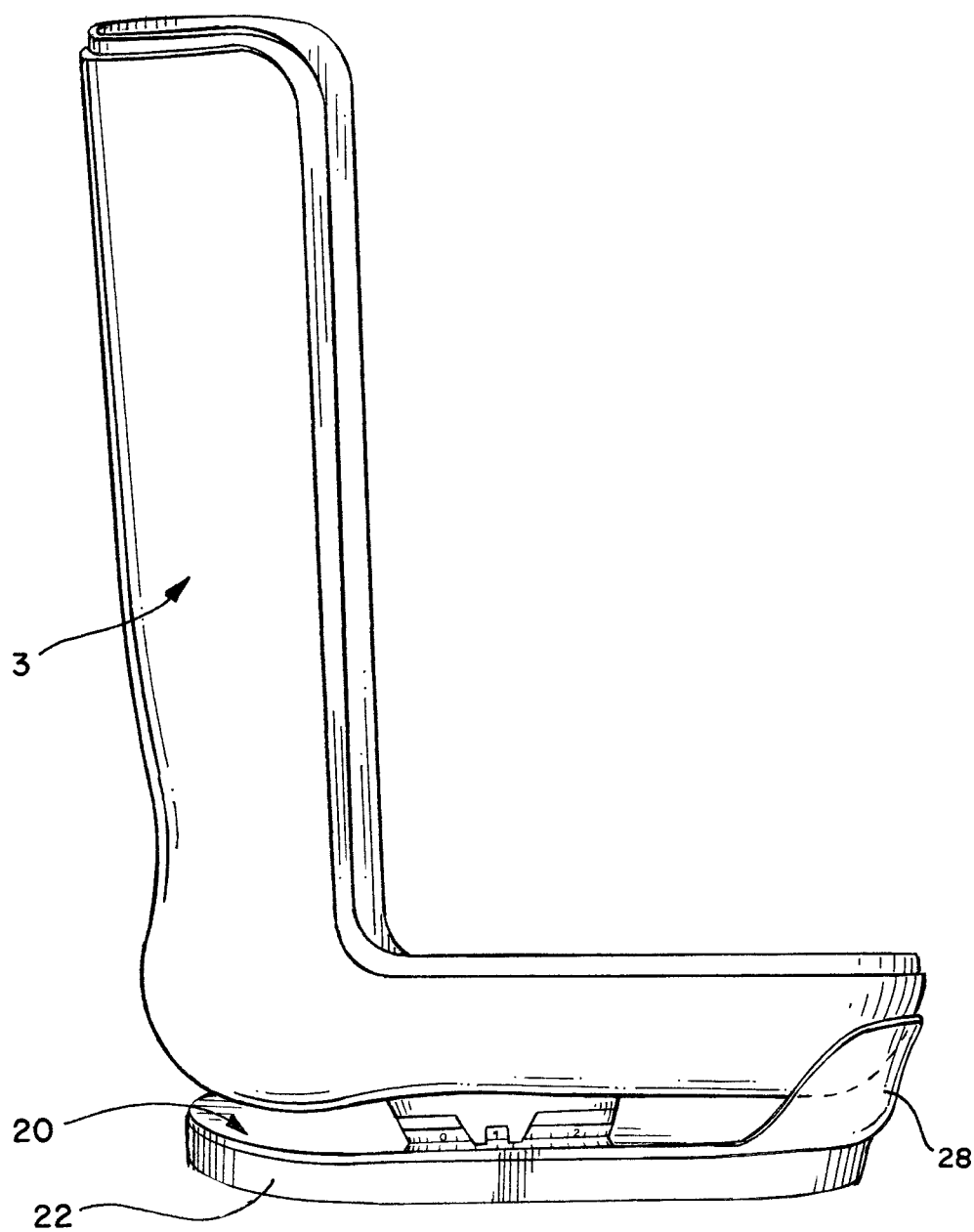
FIG. 17 is a schematic drawing of a guard shield to prevent access to a gap between the bottom of the boot and the foot plate.

FIG. 17 is a schematic sketch for an ankle/foot orthosis boot having a protective shield 28 filling the front portion of the gap between the boot and the rigid foot plate 20 of the adjustable walking sole. Accordingly, the open space between the boot 3 and the upper surface of the rigid foot plate 20 mounts the protective shield 28 to prevent any inadvertent catching of any extraneous article that could trip the patient.

Figure 18:
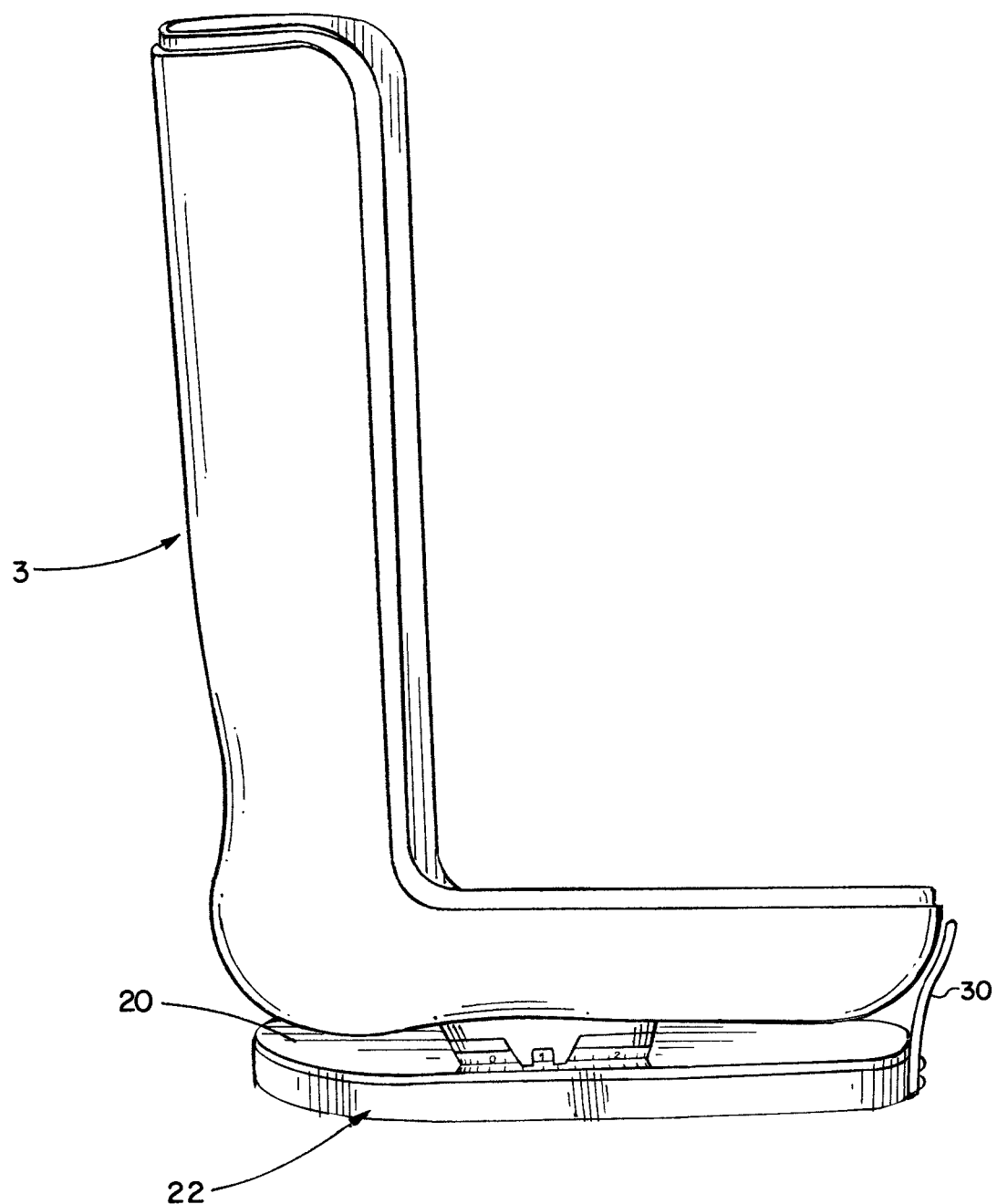
FIG. 18 is a schematic drawing of a removable front guard member to deflect access to the gap between the bottom of the boot and the foot plate.

FIG. 18 is an alternative protective guard 30 mounted on the sole 22 to extend upward in front of the boot 3 to prevent any extraneous article from entering the space between the boot and the upper surface of the boot 3 and the upper surface of the rigid foot plate 20 to prevent any extraneous article catching the open space and tripping the patient.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. An ankle/foot orthosis with an adjustable sole, comprising:
   an orthosis boot for attachment to a user's foot;
   a sole positioned offset from the orthosis boot; and
   an adjuster unit attached to the orthosis boot and the sole for providing angular adjustments of an inclination of the sole relative to the orthosis boot to provide appropriate lateral and interior/posterior angular adjustments to accommodate the specific condition of the user's foot wherein the adjuster unit includes a pair of wedged rotary plates that can be relatively moved and affixed to each other to provide a corrective alignment of the user's foot relative to a support surface and further including spring washer providing a force to separate the wedged rotary plates.

2. The ankle/foot orthosis of claim 1 further including a rigid foot plate attached to the sole with angular markings on its surface to set the sole in a forward plane of gait progression of the user.

3. The ankle/foot orthosis of claim 2 further including a front guard member extending from the foot plate across a gap to a toe portion of the orthosis boot to defeat access to the gap from extraneous objects that could trip the user.

4. The ankle/foot orthosis of claim 1 further including a bolt passing through the wedged rotary plates and the sole and secured above a bottom surface of the sole that will contact the support surface.

5. The ankle/foot orthosis of claim 4 wherein one of the wedged rotary plates has a series of radial slots and the other wedged rotary plate has a series of radial protrusions of a size to fit within the radial slots in order to set and maintain a predetermined inclination of the orthosis boot for a selected alignment of indicia on the wedged rotary plates within the indicator window.

6. The ankle/foot orthosis of claim 5 wherein the rigid foot plate can support the sole and have visible indicia to enable the indicator to align with the indicia for alignment of the orthosis boot.

7. The ankle/foot orthosis of claim 1 including an outside plate is positioned on a bottom surface of the orthosis boot to provide an indicator window adjacent side surfaces of the wedged rotary plates, wherein the respective wedged rotary plates each have indicia visible in the indicator window to enable relative movement and fixation for providing appropriate lateral and interior/posterior angular adjustments by relative rotation of the respective wedged rotary plates.

8. The ankle/foot orthosis of claim 7 wherein the outside plate can support an indicator that can be used to align the orthosis boot to accommodate a foot that is offset from a forward plane of gait progressions of the user.

9. The ankle/foot orthosis of claim 8 wherein the outside plate has a pair of recesses that can each mount the indicator to accommodate a right or left orthosis boot relative to the adjustor unit.

10. The ankle/foot orthosis of claim 7 wherein the indicator can be removable mounted on the outside plate.

11. An ankle/foot orthosis with an adjustable sole, comprising:
an orthosis boot for attachment to a user's foot;
a sole positioned offset from the orthosis boot; and
an adjuster unit attached to the orthosis boot and the sole for providing angular adjustments of an inclination of the sole relative to the orthosis boot to provide appropriate lateral and interior/posterior angular adjustments to accommodate a specific condition of the user's foot, the adjuster unit includes a pair of wedged rotary plates that can be relatively moved and affixed to each other to provide a corrective alignment of the user's foot relative to a support surface based on indicia displayed on the sides of the wedged rotary plates when aligned and displayed through an indicator and further including spring washer providing a force to separate the wedged rotary plates.

12. The ankle/foot orthosis of claim 11 further including a foot plate attached to the sole with angular markings on its surface to set the sole in a forward plane of gait progression of the user.

* * * * *